US008843355B2

(12) United States Patent
Kimura et al.

(10) Patent No.: US 8,843,355 B2
(45) Date of Patent: Sep. 23, 2014

(54) METHOD OF CONTROLLING FUEL CELL USING THE METHOD OF PREDICTING DEGRADATION OF FUEL CELL CATALYST

(71) Applicants: Hiroko Kimura, Susono (JP); Naoki Takehiro, Shizuoka-ken (JP); Manabu Kato, Susono (JP); Kazutaka Kimura, Susono (JP)

(72) Inventors: Hiroko Kimura, Susono (JP); Naoki Takehiro, Shizuoka-ken (JP); Manabu Kato, Susono (JP); Kazutaka Kimura, Susono (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 0 days.

(21) Appl. No.: 14/149,592

(22) Filed: Jan. 7, 2014

(65) Prior Publication Data
US 2014/0120435 A1 May 1, 2014

Related U.S. Application Data

(62) Division of application No. 12/751,318, filed on Mar. 31, 2010, now Pat. No. 8,660,827.

(30) Foreign Application Priority Data

Mar. 31, 2009 (JP) ................................. 2009-084428

(51) Int. Cl.
G01D 21/00 (2006.01)
G06G 7/48 (2006.01)
(Continued)

(52) U.S. Cl.
CPC .. *H01M 8/04992* (2013.01); *H01M 2008/1095* (2013.01); *Y02E 60/50* (2013.01); *G06F 17/5009* (2013.01); *G06F 15/00* (2013.01); *G01N 15/0266* (2013.01); *H01M 4/9041* (2013.01); *G01D 21/00* (2013.01); *G06F 17/10* (2013.01); *H01M 4/90* (2013.01); *G06F 19/70* (2013.01); *H01M 8/04119* (2013.01)
USPC ............................................................ 703/6

(58) Field of Classification Search
USPC .................. 703/6, 9, 11, 12; 73/866.5, 61.75; 702/128; 175/434; 428/610; 700/73
See application file for complete search history.

(56) References Cited

U.S. PATENT DOCUMENTS 6,119,510 A * 9/2000 Carasso et al. ............... 73/61.75
(Continued)

FOREIGN PATENT DOCUMENTS

JP 01122570 A 5/1989
(Continued)

OTHER PUBLICATIONS

Robert M. Darling and Jeremy P. Meyers, "Kinetic Model of Platinum Dissolution in PEMFC's," Journal of the Electrochemical Society, 150, A1523-A1527 (2003).

(Continued)

*Primary Examiner* — Kandasamy Thangavelu
(74) *Attorney, Agent, or Firm* — Gifford, Krass, Sprinkle, Anderson & Citkowski, P.C.

(57) ABSTRACT

A particle size distribution creating method includes a particle size range determining step, an integrating step of integrating the frequency of appearance of particles within the particle size range determined in the particle size range determining step, a division point determining step of determining particle sizes that provide division points, using the integral of the frequency of appearance obtained in the integrating step, and a typical point determining step of determining the minimum particle size, maximum particle size and the particle sizes of the division points as typical points. This method is characterized by assuming a particle size distribution which contains particles having the particle sizes of the respective typical points and is plotted such that the frequency of appearance of the particles having the particle size of each of the typical points is equal to the integral over each of the regions defined by the typical points, and obtaining the assumed particle size distribution as a particle size distribution model.

3 Claims, 6 Drawing Sheets

(51) Int. Cl.
*G06F 17/50* (2006.01)
*G06F 15/00* (2006.01)
*H01M 8/04* (2006.01)
*G01N 15/02* (2006.01)
*H01M 4/90* (2006.01)
*G06F 17/10* (2006.01)
*H01M 8/10* (2006.01)
*G06F 19/00* (2011.01)

(56) References Cited

U.S. PATENT DOCUMENTS

| | | | | |
|---|---|---|---|---|
| 6,136,452 | A * | 10/2000 | Munir et al. | 428/610 |
| 7,099,721 | B2 * | 8/2006 | Dunnill et al. | 700/73 |
| 2003/0084734 | A1 * | 5/2003 | Povey et al. | 73/866.5 |
| 2009/0260895 | A1 * | 10/2009 | Vail et al. | 175/434 |
| 2010/0169038 | A1 * | 7/2010 | Georgakis et al. | 702/128 |

FOREIGN PATENT DOCUMENTS

| | | |
|---|---|---|
| JP | 08162133 A | 6/1996 |
| JP | 2003197205 A | 7/2003 |
| JP | 2006139935 A | 6/2006 |
| JP | 2007103115 A | 4/2007 |
| JP | 2007190454 A | 8/2007 |
| JP | 2009063565 A | 3/2009 |

OTHER PUBLICATIONS

Robert M. Darling and Jeremy P. Meyers, "Mathematical Model of Platinum Movement in PEM Fuel Cells," Journal of the Electrochemical Society, 152, A242-A247 (2005).

Wu Bi and Thomas F. Fuller, "Modeling of PEM Fuel Cell Pt/C Catalyst Degradation," Journal of Power Sources 178, 188-196 (2008).

* cited by examiner

METHOD OF CONTROLLING FUEL CELL USING THE METHOD OF PREDICTING DEGRADATION OF FUEL CELL CATALYST

INCORPORATION BY REFERENCE

This application is a divisional application of U.S. application Ser. No. 12/751,318, filed on Mar. 31, 2010, which claims priority of Japanese Patent Application No. 2009-084428 filed on Mar. 31, 2009.

BACKGROUND OF THE INVENTION

1. Field of the Invention

The invention relates to a method of creating a particle size distribution model, a method of predicting degradation of a fuel cell catalyst, using the method of creating the particle size distribution model, and a method of controlling a fuel cell, using the method of predicting degradation of the fuel cell catalyst.

2. Description of the Related Art

Fuel cells are operable to convert chemical energy directly into electrical energy, by supplying fuel and an oxidizing agent to two electrodes that are electrically connected, and electrochemically causing oxidation of the fuel. Unlike thermal power generation, fuel cells are free from constraints of the Carnot cycle, and thus exhibit a high energy conversion efficiency. A fuel cell generally consists of a plurality of single cells laminated or stacked together, and each of the single cells has a basic structure in the form of a membrane electrode assembly in which an electrolyte membrane is sandwiched by and between a pair of electrodes. In particular, a polymer electrolyte fuel cell using a solid polymer electrolyte membrane as the electrolyte membrane has the advantages of being easily reduced in size and operating at low temperatures, and is therefore noteworthy for its use as a portable power supply or a power supply for a mobile unit.

In the polymer electrolyte fuel cell, a reaction of the following formula (I) proceeds at the anode (fuel electrode) when hydrogen is used as the fuel.

Electrons generated in the reaction of the above formula (I) pass through an external circuit, do work at an external load, and then reach the cathode (oxidant electrode). Protons generated in the reaction of the above formula (I) transfer by electrical permeation from the anode side to the cathode side in the solid polymer electrolyte membrane while they are in a hydrated state.

Also, a reaction of the following formula (II) proceeds at the cathode when oxygen is used as the oxidizing agent.

Water formed at the cathode passes mainly through a gas diffusion layer, and is discharged to the outside. Thus, the fuel cell is a clean power generator since nothing but water is discharged from the fuel cell FIG. 9 schematically shows a cross-section of a single cell 100 of a general polymer electrolyte fuel cell when it is cut in a direction of lamination of layers. The single cell 100 includes a membrane electrode assembly 8 consisting of a solid polymer electrolyte membrane (which may be simply called an electrolyte membrane) 1 having hydrogen ion conductivity, and a cathode 6 and an anode 7 between which the electrolyte membrane 1 is sandwiched. The single cell 100 further includes separators 9 and 10 located outwardly of the electrodes (i.e., the cathode 6 and anode 7), respectively. The membrane electrode assembly 8 is sandwiched by and between the separators 9 and 10. Gas channels 11 and 12 are formed at the boundaries of the separators and the electrodes, and hydrogen gas is continuously supplied to the anode, while gas (normally, air) containing oxygen is continuously supplied to the cathode. Generally, each electrode consists of a catalyst layer and a gas diffusion layer, which are laminated in this order as viewed from the electrolyte membrane. Namely, the cathode 6 consists of a cathode catalyst layer 2 and a gas diffusion layer 4 that are laminated on each other, and the anode 7 consists of an anode catalyst layer 3 and a gas diffusion layer 5 that are laminated on each other.

One of the problems encountered in the polymer electrolyte fuel cell is voltage reduction caused by dissolution of catalyst metal in the electrodes. With regard to this problem, a mathematical model that simulates oxidation and dissolution of a platinum catalyst when it is used as a catalyst metal is discussed, and calculation results using this model are described in a non-patent document (R. M. Darling and J. P. Meyers: J. Electrochem. Soc., vol. 150, pages A1523-A1527, 2003).

In the above-identified non-patent document, the rates of reactions, i.e., oxidation and dissolution, of the platinum catalyst, are specifically discussed. However, even if the mathematical model described in this document is used, precise simulation results that agree with experimental results are not necessarily obtained, as is apparent from FIG. 1 and FIG. 5 of this document.

SUMMARY OF THE INVENTION

The invention provides a method of creating a particle size distribution model with improved preciseness, within a shortened calculation time, a method of predicting degradation of a fuel cell catalyst, using the method of creating the particle size distribution model, and a method of controlling a fuel cell, using the method of predicting degradation of the fuel cell catalyst.

A first aspect of the invention is concerned with a method of creating a particle size distribution model that simulates a particle size distribution of a cluster of particles of a catalyst metal of a fuel cell, which includes a plurality of particles of the catalyst metal. The particle size distribution model creating method includes the steps of: determining a particle size range by determining a minimum particle size and a maximum particle size of the cluster of particles of the catalyst metal to be simulated, integrating the frequency of appearance of the particles in the determined particle size range, over an integration region defined by the minimum particle size as a starting point and the maximum particle size as an endpoint, dividing the integration region into a given number of regions through a first dividing operation, using the integral of the frequency of appearance, so that integrals obtained for the individual regions into which the integration region is divided are substantially equal, and determining particles sizes of division points at which the integration region is divided, determining the minimum particle size, the maximum particle size and the particle sizes of the respective division points, as typical points, and obtaining a particle size distribution model by assuming a particle size distribution containing particles having the particle sizes of the respective typical points, the particle size distribution being plotted such that the frequency of appearance of the particles having the particle size of each of the typical points is equal to the integral obtained for each of the regions into which the integration region is divided at the typical points.

In the particle size distribution model creating method as described above, the particle size distribution is determined, using the minimum particle size, the maximum particle size, and the respective points at which the integral of the frequency of appearance is equally or evenly divided, as typical points. It is thus possible to create a particle size distribution model that can precisely simulate a particle size distribution obtained by experiment, with a reduced number of variables, as compared with the particle size distribution model of the related art.

A second aspect of the invention is concerned with a method of predicting degradation of a catalyst metal of a fuel cell. The degradation predicting method includes the steps of: determining a particle size range by determining a minimum particle size and a maximum particle size of a cluster of particles of the catalyst metal of which a particle size distribution is to be simulated, the cluster of particles including a plurality of particles of the catalyst metal, integrating the frequency of appearance of the particles in the determined particle size range, over an integration region defined by the minimum particle size as a starting point and the maximum particle size as an endpoint, dividing the integration region into a given number of regions through a first dividing operation, using the integral of the frequency of appearance, so that integrals obtained for the individual regions into which the integration region is divided are substantially equal, and determining particles sizes of division points at which the integration region is divided, determining the minimum particle size, the maximum particle size and the particle sizes of the respective division points, as typical points, obtaining a particle size distribution model by assuming a particle size distribution containing particles having the particle sizes of the respective typical points, the particle size distribution being plotted such that the frequency of appearance of the particles having the particle size of each of the typical points is equal to the integral obtained for each of the regions into which the integration region is divided at the typical points, and predicting degradation of the catalyst metal of the fuel cell, using the particle size distribution model.

According to the method of predicting degradation of the fuel cell catalyst as described above in which the above-described particle size distribution model creating method is used for prediction of degradation of the fuel cell catalyst, degradation of the fuel cell catalyst which is more likely to occur in reality can be precisely simulated within the same calculation time, as compared with the case where the particle size distribution model of the related art is used for prediction of degradation of the fuel cell catalyst. Also, according to the method of predicting degradation of the fuel cell catalyst of the invention in which the above-described particle size distribution model creating method is used for prediction of degradation of the fuel cell catalyst, it is possible to provide results having the same or equivalent preciseness as results obtained when the particle size distribution model of the related art is used for prediction of degradation of the fuel cell catalyst, within a shorter time than that required in the related art.

A third aspect of the invention is concerned with a method of controlling a fuel cell. The control method includes the steps of: determining a particle size range by determining a minimum particle size and a maximum particle size of a cluster of particles of the catalyst metal of which a particle size distribution is to be simulated, the cluster of particles including a plurality of particles of the catalyst metal, integrating the frequency of appearance of the particles in the determined particle size range, over an integration region defined by the minimum particle size as a starting point and the maximum particle size as an endpoint, dividing the integration region into a given number of regions through a first dividing operation, using the integral of the frequency of appearance, so that integrals obtained for the individual regions into which the integration region is divided are substantially equal, and determining particles sizes of division points at which the integration region is divided, determining the minimum particle size, the maximum particle size and the particle sizes of the respective division points, as typical points, obtaining a particle size distribution model by assuming a particle size distribution containing particles having the particle sizes of the respective typical points, the particle size distribution being plotted such that the frequency of appearance of the particles having the particle size of each of the typical points is equal to the integral obtained for each of the regions into which the integration region is divided at the typical points, predicting degradation of the catalyst metal of the fuel cell, using the particle size distribution model, measuring a cell voltage of the fuel cell, measuring a cell resistance of the fuel cell, determining whether humidity control of the fuel cell is to be performed, based on a degree of the predicted degradation of the catalyst metal of the fuel cell, the measured cell voltage, and the measured cell resistance, and selecting and executing a first control mode in which control for reducing the humidity of the fuel cell is performed if the measured cell resistance is smaller than a predetermined resistance value, a second control mode in which control for increasing the humidity of the fuel cell is performed if the measured cell resistance is equal to or larger than the predetermined resistance value, and a third control mode in which control for increasing the humidity of the fuel cell is performed if it is predicted, from a result of degradation prediction of the catalyst metal of the fuel cell, that a surface area of a local portion of the fuel cell catalyst is reduced.

According to the present invention, the particle size distribution is determined, using the minimum particle size, the maximum particle size, and the respective points at which the integral of the frequency of appearance is equally or evenly divided, as typical points. It is thus possible to create a particle size distribution model that can precisely simulate a particle size distribution obtained by experiment, with a reduced number of variables, as compared with the particle size distribution model of the related art.

BRIEF DESCRIPTION OF THE DRAWINGS

The foregoing and further features and advantages of the invention will become apparent from the following description of example embodiments with reference to the accompanying drawings, wherein like numerals are used to represent like elements and wherein.

DETAILED DESCRIPTION OF EMBODIMENTS

A particle size distribution model creating method of the invention, which is a method of creating a particle size distribution model that simulates a particle size distribution of a cluster of particles as a collection of a plurality of particles having different particle sizes, includes a particle size range determining step of determining the minimum particle size and maximum particle size of the particles included in the cluster of particles to be simulated, an integrating step of integrating the frequency of appearance of the particles within the particle size range determined in the particle size range determining step, over an integration region defined by the minimum particle size as a starting point and the maximum particle size as an endpoint, a division point determining step of dividing the integration region used in the integrating step into a given number of regions through a first dividing operation, using the integral of the frequency of appearance obtained in the integrating step, so that the integrals over the individual regions into which the integration region is divided are substantially equal, and determining particles sizes of division points at which the integration region is divided, and a typical point determining step of determining the minimum particle size, the maximum particle size and the particle sizes of the respective division points, as typical points. The model creating method is characterized by assuming a particle distribution which contains particles having the particle sizes of the respective typical points, and is plotted such that the frequency of appearance of the particles having the particle size of each of the typical points is equal to the integral obtained for each of the regions into which the integration region is divided at the typical points, and obtaining the assumed particle size distribution as a particle size distribution model.

Figure 4:
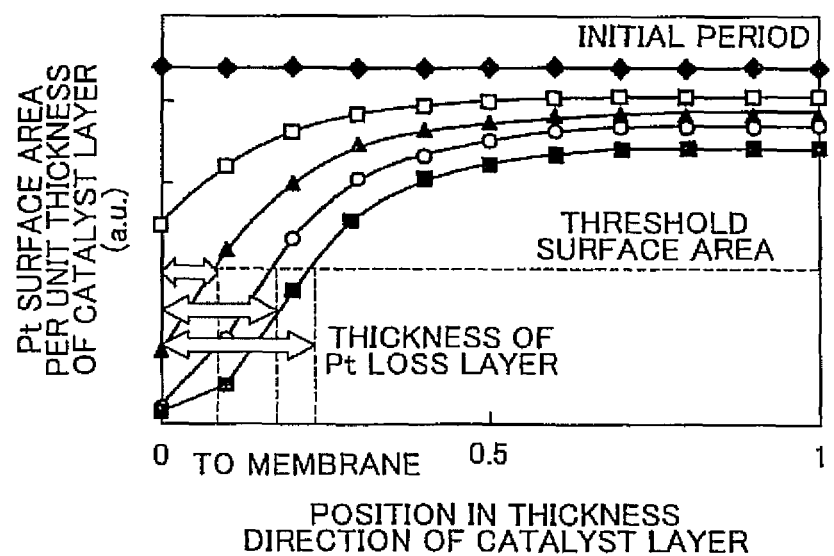
FIG. 4 is a graph showing examples of calculation results indicating prediction results obtained in a fuel cell catalyst degradation predicting step of the invention.

Some examples of techniques for measuring a particle size distribution of a platinum catalyst by experiment have been reported in the related art. For example, an article of H. A. Gasteiger et al.: J. Electrochem. Soc., vol. 152, pages A2256-A2271, 2005 (which will be called "Article 1") discusses measuring the surface area of particles of the platinum catalyst as well as measuring the particle size distribution of the platinum catalyst. In Article 1, a graph (FIG. 7 of Article 1) showing the actually measured particle size distribution of the platinum catalyst in a cathode of a membrane electrode assembly, and a graph (FIG. 4 of Article 1) showing measurement results of the surface area of the platinum catalyst are provided. The graph of FIG. 7 of Article 1, in which the horizontal axis indicates the catalyst particle size and the vertical axis indicates the number of particles, shows measurement results of particle sizes of 200 spherical particles selected from platinum catalyst particles in the initial state of the fuel cell, and 200 spherical particles selected from platinum catalyst particles after power generation. All of the particles sizes of the selected particles were measured through observation with a transmission electron microscope (TEM). The particle size distribution of the platinum catalyst particles (the average particle size=5.9 nm) after power generation has a smaller height and a larger width, in other words, is in a broad condition, as compared with the particle size distribution of the platinum catalyst particles (the average particle size=2.8 nm) of the initial state. This phenomenon occurs because dissolution of the platinum catalyst proceeds as the operating time of the fuel cell passes, resulting in a further reduction of the particles sizes of relatively small particles due to the dissolution, and the agglomeration of dissolved platinum and particles having relatively large particle sizes occurs, resulting in a further increase in the particle size. In the graph of FIG. 4 of Article 1, the horizontal axis indicates the number of power generation cycles, and the vertical axis indicates a total surface area of the catalyst particles. As is understood from FIG. 7 as described above, the dissolution of the platinum catalyst causes the agglomeration of dissolved platinum and particles having relative large particle sizes; therefore, the total surface area of the catalyst particles decreases as the number of power generation cycles increases. As the total surface area of the catalyst particles decreases, a catalyst reaction field that governs a reaction at the electrode of the fuel cell is reduced, resulting in degradation of the fuel cell catalyst.

If the particle size distribution of the platinum catalyst obtained by measurement/experiment as described above is used for predicting degradation of the fuel cell catalyst, simulation results cannot be obtained within a practical calculation time. This is because the particle size distribution of platinum particles is actually a continuous distribution, and therefore, an enormously large number of data points are required to achieve precise simulation.

Figure 7:
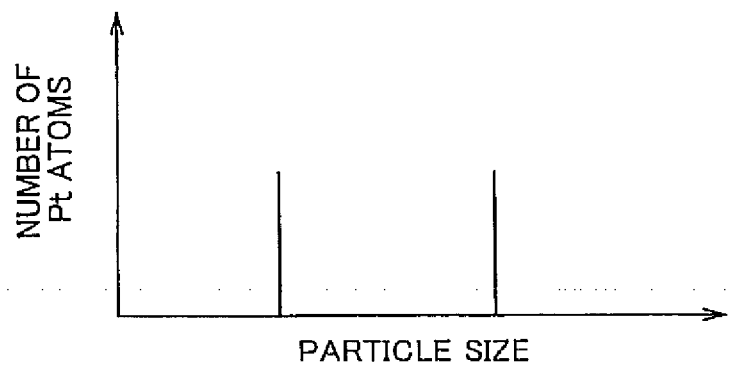
FIG. 7 is a graph schematically showing a platinum catalyst particle size distribution, which is simplified and taken into a calculation model in the related art.

In the meantime, an article of W. Bi and T. F. Fuller: J. Power Sources, vol. 18, pages 188-196, 2008 (which will be called "Article 2") discusses simplifying a platinum catalyst particle size distribution, and incorporating it into a calculation model. FIG. 7 is a graph schematically showing the platinum catalyst particle size distribution discussed in Article 2. In the graph of FIG. 7, the horizontal axis indicates the particle size, and the vertical axis indicates the number of platinum atoms. As is understood from FIG. 7, the platinum catalyst particle distribution model discussed in Article 2 is represented by two types of platinum particles having different particle sizes, without taking account of changes in the number of particles. In Article 2, a graph (FIG. 3 of Article 2) is provided in which the horizontal axis indicates the operating time and the vertical axis indicates the total surface area of catalyst particles. As is understood from FIG. 3 of Article 2, two graphs (graphs indicated by solid lines in FIG. 3 of Article 2) indicating simulation results using the model as shown in FIG. 7 do not match or agree with a graph (graph indicated by a broken line in FIG. 3 of Article 2) indicating results obtained by experiment. This is because the surface area of the platinum particles does not change continuously, due to the use of the particle size distribution model represented by two types of platinum particles having different particle sizes without taking account of changes in the number of particles.

Figure 8A:
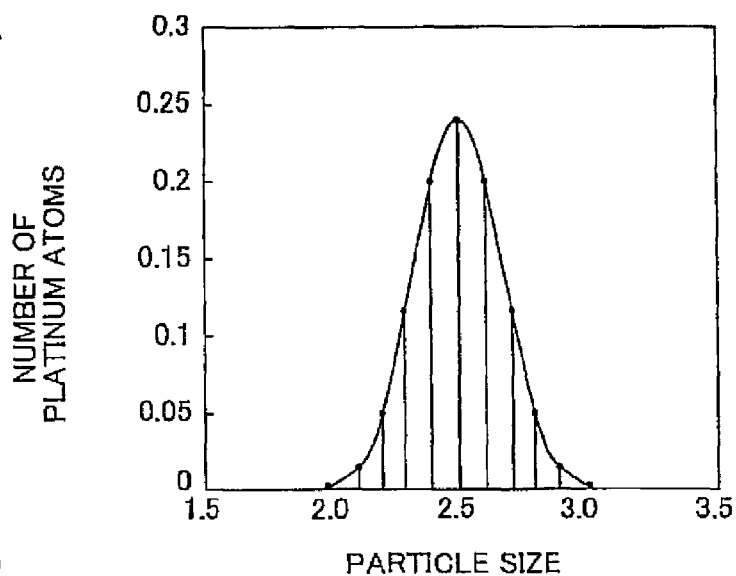
FIG. 8A is a schematic view of a platinum catalyst particle size distribution model used in a comparative example.
Figure 8B:
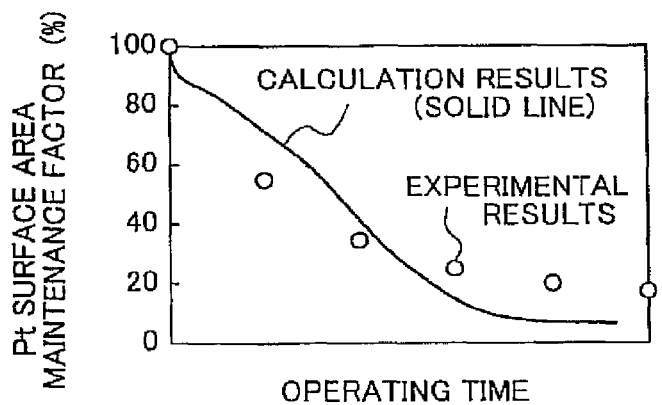
FIG. 8B is a graph indicating the platinum surface area maintenance factor with respect to the operating time (the number of power generation cycles)
Figure 9:
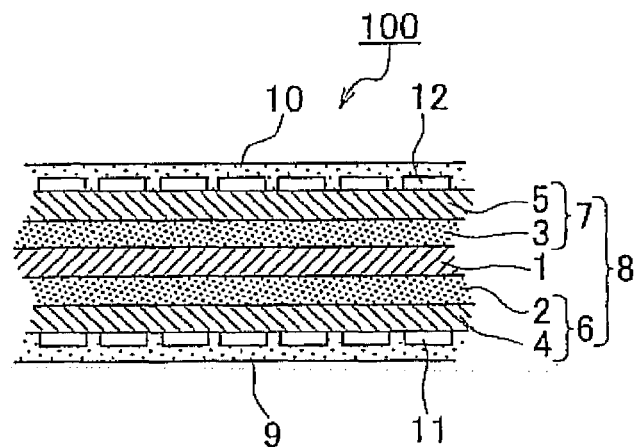
FIG. 9 is a view schematically showing a cross-section of a single cell of a general polymer electrolyte fuel cell when cut in a direction of lamination of layers.

FIG. 8A is a graph schematically showing a particle size distribution model as an application of the platinum catalyst particle size distribution discussed in Article 2. In FIG. 8A, the vertical axis and horizontal axis indicate the same parameters as those of FIG. 7. As is understood from FIG. 8A, the particle size distribution model of FIG. 8A simulates the actual particle size distribution (indicated by a curve in FIG. 8A) as shown in FIG. 7 of Article 1. In the particle size distribution model (vertical straight lines in FIG. 8A), a number of particle sizes in the particle size distribution are selected, such that the particle sizes are spaced at equal intervals on the horizontal axis, and the number of particles having each particle size changes along the horizontal axis. FIG. 8B is a graph in which the horizontal axis indicates the operating time, and the vertical axis indicates the total surface area of catalyst particles. As is understood from FIG. 8B, a graph (solid line) indicating simulation results using the model shown in FIG. 8A does not match or agree with plots indicating results obtained by experiment. Accordingly, it is found difficult to simulate the results obtained by experiment, with the particle size distribution model as a mere application of the related art. Thus, the known methods cannot reproduce an exponential reduction of the platinum catalyst surface area, which is observed by experiment over a long period of operating time of the fuel cell. The present invention provides a method of creating a precise particle size distribution model within a reduced calculation time, using differences of particles sizes of different particles as variables, unlike the particle size distribution model creating method of the related art as described above.

The "frequency of appearance" mentioned above in relation to the invention may be represented by the number of particles, mass, or volume. When the frequency of appearance is represented by the number of particles, the particle size distribution becomes a left-right symmetrical distribution (for example, a normal distribution), as shown in FIG. 7 of the above-described Article 1. When the frequency of appearance is represented by mass or volume, the particle size distribution is not a left-right symmetrical, normal distribution, but an asymmetrical distribution, since the mass or volume generally increases as the particle size increases. However, such a particle size distribution does not cause any problem when a long-term operation is simulated, even though slight errors or deviations from experimental values appear in the initial period of the operating time.

The method of creating a particle size distribution model according to the invention includes at least the particle size range determining step, integrating step, division point determining step, and the typical point determining step. The particle size range determining step to be performed first is a step of determining the minimum particle size and maximum particle size of particles included in a cluster of particles to be simulated. In this step, the average particle size as well as the minimum particle size and the maximum particle size may be determined.

The integrating step to be performed subsequent to the particle size range determining step is a step of integrating the frequency of appearance of particles within the particle size range determined in the particle size range determining step, over an integration region from the minimum particle size as a starting point to the maximum particle size as an end point. In the integrating step, the sum of the frequencies of appearance of all of the particles in the particle size range determined in the particle size range determining step can be calculated.

Figure 1A:
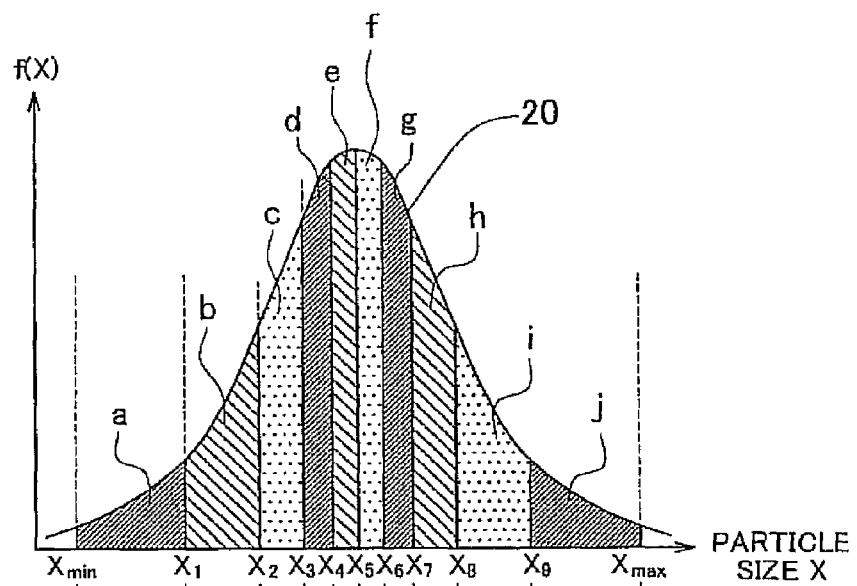
FIG. 1A is a schematic view specifically showing a division point determining step of the invention.

The division point determining step to be performed subsequent to the integrating step is a step of dividing the integration region used in the integrating step into a given number of regions through a first dividing operation, using the integral of the frequency of appearance obtained in the integrating step, so that integrals obtained for the individual regions into which the integration region is divided are equal. FIG. 1A is a schematic view specifically showing the division point determining step of the invention. More specifically, FIG. 1A is a graph in which the vertical axis indicates the frequency f(x) of appearance, and the horizontal axis indicates the particle size x, while a curve 20 represents the actual particle distribution (normal distribution). When the division point determining step is executed, the minimum particle size $x_{min}$ and maximum particle size $x_{max}$ of particles included in the cluster of particles to be simulated have already been determined in the above-described particle size range determining step. Also, the integral (the area of a range defined by the curve 20 and the horizontal axis) has already been determined in the above-described integrating step, by integrating the frequency of appearance of the particles over the range from the minimum particle size $x_{min}$ as a starting point to the maximum particle size $x_{max}$ as an end point. In FIG. 1A, the integration region is divided into 10 regions through the first dividing operation, using the above-mentioned integral, so that area a=area b=area c= . . . =area i=area j in FIG. 1A. In this manner, division points $x_1, x_2, \ldots x_9$ are determined so that the integrals obtained for the individual regions defined by the division points are equal. In the typical point determining step as the last step, the particle sizes of the division points $x_1, x_2, \ldots x_9$, and the minimum particle size $x_{min}$ and the maximum particle size $x_{max}$ are determined as typical points.

In the division point determining step, a method using a probability density function as indicated below, for example, may be used as a method of actually determining the division points $x_1, x_2, \ldots x_9$. In the following, an example in which the method is applied to a normal distribution will be described. The normal distribution has a probability density function as expressed by the following equation (1). In the equation (1), x denotes a probability variable, µ denotes an average value, and σ denotes a variance.

$$f(x) = \frac{1}{\sqrt{2\pi\sigma^2}} \exp\left(\frac{-(x-\mu)^2}{2\sigma^2}\right), \tag{1}$$

$$-\infty < x < \infty, \sigma^2 > 0$$

A cumulative distribution function F(X) using the probability density function f(x) is represented by the following equation (2).

$$F(X) = \int_{-\infty}^{X} f(x)dx \tag{2}$$

Figure 2:
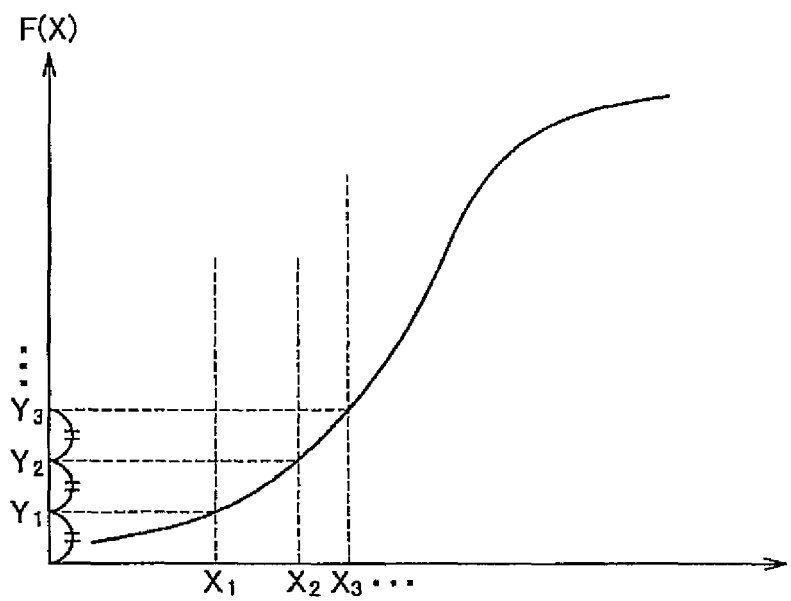
FIG. 2 is a graph schematically showing a cumulative distribution function $F(X)$.

When an inverse function of the cumulative distribution function F(X) is denoted as $F^{-1}(X)=G(Y)(=X)$, values of $X_1, X_2, \ldots X_n$ are obtained with respect to values of $Y_1, Y_2, \ldots Y_n$, by using the inverse function. The values of $Y_1, Y_2, \ldots Y_n$ may be determined, for example, in the following manner. FIG. 2 is a graph schematically showing the cumulative distribution function F(X). By placing $Y_1, Y_2, \ldots Y_n$ at equal intervals on the F(X) axis, $X_1, X_2, \ldots X_n$ corresponding to $Y_1, Y_2, \ldots Y_n$ can be obtained. The $X_1, X_2, \ldots X_n$ obtained through this operation can be adopted as division points.

In fact, it is extremely difficult to obtain the inverse function by manual calculation. On the other hand, the inverse function of the cumulative distribution function F(X) may be easily obtained by software, such as spreadsheet software. For example, with the use of Microsoft Office Excel (trade name, manufactured by Microsoft) as one type of spreadsheet software, values of $X_1, X_2, \ldots X_n$ can be obtained by using a NORMSINV function that returns values of the inverse function of the cumulative distribution function of a standard normal distribution, or a NORMINV function that returns values of the inverse function of the cumulative distribution function of a normal distribution with respect to the designated average and standard deviation.

Figure 1B:
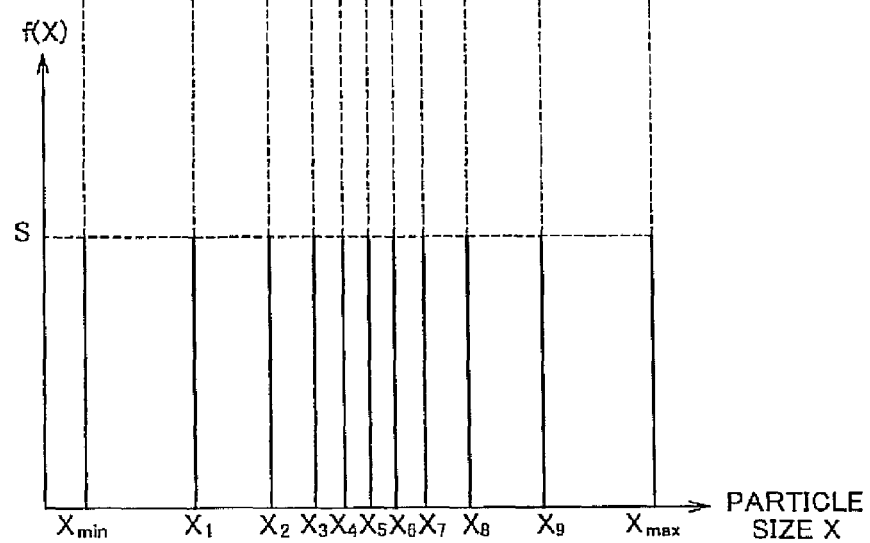
FIG. 1B is a graph schematically showing a particle size distribution model created by a creating method of the invention.

Considering that the more precise particle size distribution can be reproduced by dividing a part of the region or the entire region into further smaller regions, one form of the particle size distribution model creating method of the invention may be configured such that, in the division point determining step, a part of or all of the given number of regions into which the determined particle size range is divided through the first dividing operation is divided further into a given number of regions, such that the integrals obtained for the individual regions resulting from the second dividing operation are equal, and the particle sizes that provide the division points in the first and second dividing operations are determined. In particular, as one form of the particle size distribution model creating method of the invention, which is useful for investigating changes in the particle size distribution over a long period of time, the second dividing operation may be performed on a region including the maximum particle size, out of the given number of regions into which the determined particle size range is divided through the first dividing operation, for the reasons as follows. As described above with reference to FIG. 7 of Article 1, particles having relatively small particle sizes dissolve in a very short time, and the agglomeration of these particles and other particles occurs; therefore, it is not necessary to keep track of the behaviors of these particles particularly in detail when changes in the particle size distribution over a considerably long period of time are predicted. On the other hand, it is particularly important to keep track of the behaviors of particles having relatively large particle sizes when changes in the particle size distribution over a considerably long period of time are predicted. However, as shown in FIG. 1B as described above, only one typical point exists, in particular, in the region including the maximum particle size, which is not necessarily sufficient to keep track of detailed changes in the particle size distribution. Accordingly, the region including the maximum particle size (the region having area j in FIG. 1A) is further divided into a given number of regions so that integrals for the individual regions are equal, thereby to provide the particle size distribution model useful for investigating changes in the particle size distribution over a long period of time.

FIG. 1B is a graph schematically showing a particle size distribution model created by the creating method of the invention. In the graph of FIG. 1B, the vertical axis indicates the frequency of appearance, and the horizontal axis indicates the particle size x. The particle size distribution model shown in FIG. 1B contains particles having each of the particle sizes $x_1, x_2, \ldots x_9$ determined in the typical point determining step, and the minimum particle size $x_{min}$ and the maximum particle size $x_{max}$, and assumes a particle size distribution in which the frequency of appearance of particles having the particle size of each typical point is equal to the integral S of each of the regions defined by the typical points. Thus, the points at which the integral of the frequency of appearance is equally divided, the minimum particle size and the maximum particle size are used as the typical points; therefore, the particle size distribution model created by the particle size distribution model creating method according to the invention can precisely simulate the particle size distribution obtained by experiment, with a reduced number of variables, as compared with the particle size distribution model of the related art.

As one form of the particle size distribution model creating method of the invention, the particle size distribution may be in the form of a normal distribution since the particle size distribution can be more precisely reproduced by use of the normal distribution. It is, however, to be understood that the particle size distribution is not limited to the normal distribution, but various probability distributions may be used provided that the actual particle size distribution can be precisely reproduced. While the types of probability distributions include discrete distribution type, absolute discrete distribution type, and continuous distribution type, it is preferable to use a probability distribution of continuous type since one of the main objects of the invention is to predict degradation of a fuel cell catalyst, and the actual distribution of catalyst particles is a continuous distribution. Examples of the probability distribution of continuous type include, for example, a logarithmic normal distribution, exponential distribution, t-distribution, chi-square distribution, gamma distribution, beta distribution, F-distribution, Cauchy distribution, Erlang distribution, triangular distribution, Laplace distribution, Rayleigh distribution, logistic distribution, Pareto distribution, Weibull distribution, and functions referring to the actually measured platinum particle size distribution.

A method of predicting degradation of the fuel cell catalyst according to the invention is characterized by including a step of creating a particle size distribution model of the fuel cell catalyst, using the above-described particle size distribution model, and a step of predicting degradation of the fuel cell catalyst, using the particle size distribution model of the fuel cell catalyst.

The method of predicting degradation of the fuel cell catalyst of the invention has the particle size distribution model creating step and the step of predicting degradation of the fuel cell catalyst (which will be called "fuel cell catalyst degradation predicting step"). Of these steps, the particle size distribution model creating step has already been described in the explanation of the particle size distribution model creating method of the invention.

In the fuel cell catalyst degradation predicting step according to the invention, the above-described particle size model creating method is used for prediction of degradation of the fuel cell catalyst; therefore, degradation of the fuel cell catalyst which is more likely to occur in real operating situations can be precisely simulated within the same calculation time, as compared with the case where the particle size distribution model of the related art is used for prediction of degradation of the fuel cell catalyst. Also, in the fuel cell catalyst degradation predicting step of the invention, the use of the above-described particle size distribution model creating method for prediction of degradation of the fuel cell catalyst makes it possible to yield results having substantially the same degree of preciseness as results provided when the particle size distribution model of the related art is used for prediction of degradation of the fuel cell catalyst, within a shorter time than that of the related art.

In one form of the fuel cell catalyst degradation predicting method of the invention, at least one mathematical model selected from a mathematical model indicative of the rate of platinum dissolution reaction, a mathematical model indicative of the rate of platinum oxidation reaction, and a mathematical model indicative of material balance may be used. Of the above-indicated mathematical models, all of the mathematical model indicative of the rate of platinum dissolution reaction, mathematical model indicative of the rate of platinum oxidation reaction, mathematical model indicative of the rate of dissolution of platinum oxide (II) and the mathematical model indicative of material balance may be used in the fuel cell catalyst degradation predicting step.

Table 1 below shows the meanings of symbols used in the mathematical models used in the fuel cell catalyst degradation predicting step of the invention.

TABLE 1

| Symbol | Unit | Meaning |
|---|---|---|
| $C_{H+}$ | mol/l | proton concentration |
| $C_{H+,ref}$ | — | coefficient conversion constant of $C_{H+}$ 1 mol/l→mol/cm³(1/1000) |
| $C_{Pt2+}$ | mol/l | Pt ion concentration |
| $C_{Pt2+,ref}$ | — | coefficient conversion constant of $C_{Pt2+}$ 1 mol/l→mol/cm³(1/1000) |
| $D_{Pt2+}$ | cm²/sec | diffusion coefficient of Pt ions (1E-6 cm²/sec, from Document 2) |
| F | C/equiv | Faraday constant (96485 C equiv⁻¹) |
| $k_1$ | mol/(cm²sec) | rate constant of Pt dissolution |
| $k_2$ | mol/(cm²sec) | rate constant of Pt oxidation |
| $k_3$ | mol/(cm²sec) | rate constant of PtO dissolution |
| $M_{Pt}$ | g/mol | weight of Pt atom (195 g/mol) |
| $M_{PtO}$ | g/mol | weight of PtO atom (211.09 g/mol) |
| $n_1$ | equiv/mol | number of electrons involved in Pt dissolution (2 equiv/mol) |
| $n_2$ | equiv/mol | number of electrons involved in Pt oxidation (2 equiv/mol) |
| R | J/(mol · K) | gas constant (8.314J/(mol · K)) |
| R(i, z) | cm | Pt particle radius |
| T | K | temperature |
| $U_1$ | V | thermokinetic reversible potential of Pt dissolution |
| $U_2$ | V | thermokinetic reversible potential of Pt oxidation |
| $U^{\theta}_1$ | V | standard thermokinetic potential of Pt dissolution |
| $U^{\theta}_2$ | V | standard thermokinetic potential of Pt oxidation |
| $\alpha_{a,1}$ | — | anodic transfer coefficient of Pt dissolution |
| $\alpha_{a,2}$ | — | anodic transfer coefficient of Pt oxidation |
| $\alpha_{c,1}$ | — | cathodic transfer coefficient of Pt dissolution |
| $\alpha_{c,2}$ | — | cathodic transfer coefficient of Pt oxidation |
| $\rho_{Pt}$ | g/cm³ | density of Pt (21.95 g/cm³) |
| $\rho_{PtO}$ | g/cm³ | density of PtO (14.1 g/cm³) |
| $\omega$ | J/mol | PtO-PtO interaction coefficient |
| $\theta_{vac}$ | — | proportion of Pt surface not covered with oxide |
| $\theta_{PtO}$ | — | proportion of Pt surface covered with oxide |
| $\sigma_{Pt}$ | J/cm² | surface tension of Pt particles |
| $\sigma_{PtO}$ | J/cm² | surface tension of PtO particles |
| E | V | cell potential |
| $\Delta\mu^0_{PtO}$ | J/mol | chemical potential shift of PtO |

The following equation (3) may be used as a mathematical model indicative of the rate of platinum dissolution reaction.

$$r_1(i, z) = k_1 \theta_{vac}(i, z) \left[ \begin{array}{c} \exp\left(\frac{\alpha_{a,1} n_1 F}{RT}(E - U_1(i, z))\right) - \\ \left(\frac{C_{Pt2+}(z)}{C_{Pt2+,ref}}\right) \exp\left(-\frac{\alpha_{c,1} n_1 F}{RT}(E - U_1(U_1(i, z)))\right) \end{array} \right] \quad (3)$$

In the above equation (3), i is the number of types of particles having different radii (the same definition applies to the equations below). The potential $U_1(i, z)$ in the above equation (3) is defined by the following equation (3a).

$$U_1(i, z) = U^{\theta}_1 - \frac{\Delta\mu_{Pt}(i, z)}{2F} \quad (3a)$$

The term $\Delta\mu_{Pt}(i, z)$ in the above equation (3a) is defined by the following equation (3b).

$$\Delta\mu_{Pt}(i, z) = \frac{\sigma_{Pt} M_{Pt}}{R(i, z)\rho_{Pt}} \quad (3b)$$

The following equation (4) may be used as a mathematical model indicative of the rate of platinum oxidation reaction.

$$r_2(i, z) = k_2 \left[ \begin{array}{c} \exp\left(-\frac{\omega \theta_{PtO}(i, z)}{RT}\right)\exp\left(\frac{\alpha_{a,2} n_2 F}{RT}(E - U_2(i, z))\right) - \\ \theta_{PtO}(i, z)\left(\frac{C^2_{H+}}{C^2_{H+,ref}}\right)\exp\left(-\frac{\alpha_{c,2} n_2 F}{RT}(E - U_2(i, z))\right) \end{array} \right] \quad (4)$$

The potential $U_2(i, z)$ in the above equation (4) is defined by the following equation (4a).

$$U_2(i, z) = U^{\theta}_2 + \frac{\Delta\mu_{PtO}(i, z)}{2F} - \frac{\Delta\mu_{Pt}(i, z)}{2F} \quad (4a)$$

The term $\Delta\mu_{PtO}(i, z)$ in the above equation (4a) is defined by the following equation (4b).

$$\Delta\mu_{PtO}(i, z) = \Delta\mu^0_{PtO} + \frac{\sigma_{PtO} M_{PtO}}{R(i, z)\rho_{PtO}} \quad (4b)$$

The following equation (5) may be used as a mathematical model indicative of the rate of dissolution of platinum oxide (II).

$$r_3(i, z) = k_3 \left( \theta_{PtO}(i, z) \cdot \frac{C^2_{H+}(z)}{C^2_{H+,ref}} - \frac{C_{Pt2}(z)}{C_{Pt2+,ref}} \cdot \frac{1}{K_3(i, z)} \right) \quad (5)$$

The term $K_3(i, z)$ in the above equation (5) is defined by the following equation (5a).

$$K_3(i, z) = \exp\left[\frac{F}{RT}(n_1 U_1(i, z) - n_2 U_2(i, z))\right] \quad (5a)$$

The following equation (6) is used as a mathematical model of material balance when only platinum oxide (II) is taken into consideration.

$$\frac{d\theta_{PtO}(i, z)}{dt} = \left(\frac{r_2(i, z) - r_3(i, z)}{\Gamma_{max}}\right) - \frac{2\theta_{PtO}(i, z)}{R(i, z)} \cdot \frac{dR(i, z)}{dt} \quad (6)$$

In the above equation (6), $\Gamma_{max}$ is the maximum surface coverage of platinum. The term $dR(i, z)$ in the above equation (6) is defined by the following equation (6a).

$$\frac{dR(i, z)}{dt} = -\frac{M_{Pt}}{\rho_{Pt}}(r_1(i, z) + r_2(i, z)) \quad (6a)$$

The following equation (7) may be used as a mathematical model of material balance of platinum ions (II) finally obtained.

$$\varepsilon \frac{dC_{Pt2+}(z)}{dt} = \varepsilon^{1.5} D_{Pt2+} \frac{d^2 C_{Pt2+}(z)}{dt^2} + \sum 4\pi R(i, z)^2 N(i)(r_1(i, z) + r_2(i, z)) \quad (7)$$

The above-indicated mathematical models may be applied to the fuel cell catalyst degradation predicting method of the invention, with reference to, for example, an article of R. M. Darling and J. P. Meyers: J. Electrochem. Soc., vol. 150, pages A1523-A1527, 2003, an article of R. M. Darling and J. P. Meyers: J. Electrochem. Soc., vol. 152, pages A242-A247, 2005, an article of W. Bi and T. F. Fuller: J. Power Sources, vol. 178, pages 188-196, 2008, etc.

Figure 3:
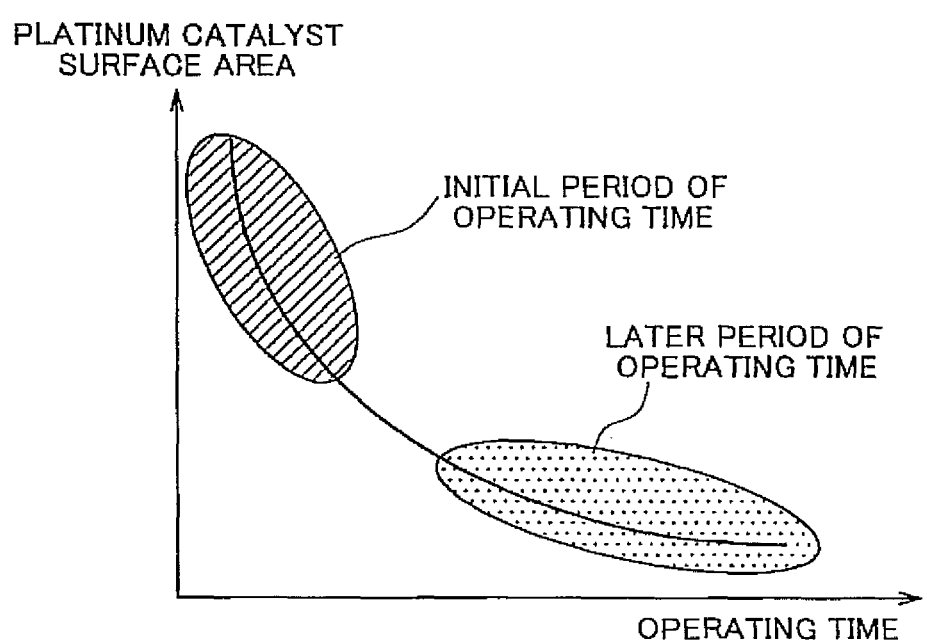
FIG. 3 is a graph schematically showing a simulation result in a first application of a method of predicting degradation of a fuel cell catalyst of the invention, wherein the horizontal axis indicates the operating time, and the vertical axis indicates the platinum catalyst surface area.

As a first application of the fuel cell catalyst degradation predicting method of the invention, this method is used in a control system of a fuel cell vehicle. FIG. 3 is a graph schematically showing simulation results in the first application. In the graph, the horizontal axis indicates the operating time, and the vertical axis indicates the platinum catalyst surface area. The oval areas in FIG. 3 represent approximate simulation zones in the initial period of the operating time and the later period of the operating time, respectively. Initially, a particle size distribution model of a fuel cell catalyst is created using the particle size distribution model creating method. Then, using the particle size distribution model and the above-indicated mathematical models, the current surface area of platinum catalyst particles is estimated from physical and chemical data, such as the initial catalyst particle size, the structure of the catalyst layer, the operating pattern and operating time up to the present, and so forth. In the initial period of the operating time as shown in FIG. 3, the surface area of the platinum catalyst particles is sharply reduced. In this stage, a higher priority is given to prolonging the life of the fuel cell performance, than to improving the fuel efficiency, and control for lowering the upper-limit potential of the fuel cell, or control for shortening the upper-limit potential holding time of the fuel cell are performed. More specifically, the upper-limit potential of the fuel cell may be controlled to 1.0V or lower, preferably, 0.9V or lower, more preferably, 0.85V or lower. In the later period of the operating time as shown in FIG. 3, the surface area of the platinum catalyst particles is reduced gently or at a lower rate. In this stage, the upper-limit potential of the fuel cell is raised in order to improve the fuel efficiency. More specifically, the upper-limit potential of the fuel cell may be controlled to 0.5V or lower, preferably, 0.7V or lower, more preferably, 0.85V or lower.

As a second application of the fuel cell catalyst degradation predicting method of the invention, a fuel cell system may be provided which informs the user of the time for maintenance, using information about the estimated condition of catalyst degradation. Initially, a particle size distribution model of the fuel cell catalyst is created using the particle size distribution model creating method. Then, using the particle size distribution model and the above-indicated mathematical models, the current surface area of platinum catalyst particles is estimated from physical and chemical data, such as the initial catalyst particle size, the structure of the catalyst layer, the operating pattern and operating time up to the present, and so forth. In the second application, if the surface area of the platinum catalyst particles is reduced, and reaches a set criterion, the system can inform the user that it is the time for maintenance. Also, in the second application, even if the surface area of the platinum catalyst particles does not reach a set criterion, the system can inform the user how long the fuel cell can be used before the time for maintenance is reached.

A method of controlling a fuel cell according to the invention is characterized by including a step of predicting degradation of the fuel cell catalyst, using the above-described fuel cell catalyst degradation predicting method, a step of measuring cell voltage of the fuel cell, a step of measuring cell resistance of the fuel cell, a humidity control determining step of determining whether humidity control of the fuel cell is to be performed, based on the result of degradation prediction obtained in the fuel cell catalyst deterioration predicting step, a value of cell voltage obtained in the cell voltage measuring step, and a value of cell resistance obtained in the cell resistance measuring step, and a step of selecting one of three control modes and performing control of the selected control mode. The three control modes include a first control mode in which control for reducing the humidity is performed when it is determined in the humidity control determining step that the value of cell resistance obtained in the cell resistance measuring step is smaller than a predetermined resistance value, a second control mode in which control for increasing the humidity of the fuel cell is performed when the value of cell resistance obtained in the cell resistance measuring step is equal to or larger than the predetermined resistance value, and a third control mode in which control for increasing the humidity of the fuel cell is performed when it is predicted from the result of degradation prediction obtained in the fuel cell catalyst degradation predicting step that the surface area of the fuel cell catalyst is reduced in a local portion of the catalyst.

Various types of degradation become causes of output reduction of the fuel cell, and an effective control method is different from one type of degradation to another. However, the type of degradation cannot be specified even if the output voltage, output current and resistance are measured, as in the related art. In the related art, therefore, adjustment of an output value, or the like, and comparison of the output with an output command current value must be continued until the optimum control method is found; therefore, correction of control cannot be effected with good response.

The causes of reduction of the output performance of the fuel cell are roughly classified into the following three types: (1) reduction of the reaction field due to excessive water caused by reduction of the draining capability (so-called flooding), (2) reduction of the catalytic activity due to reduction of the surface area of the platinum catalyst, and (3) increase of resistance to proton transfer due to the presence of a platinum loss layer. The "platinum loss layer" mentioned in the cause (3) of reduction of the output performance of the fuel cell refers to a layer that is formed in a portion of the catalyst layer close to the electrolyte membrane as the operating time of the fuel cell increases. The platinum catalyst repeats dissolution and deposition, under the influence of potential fluctuations caused by changes in the load of the fuel cell (for example, acceleration and deceleration of a mobile unit when the fuel cell is used in the mobile unit). As a result, a degradation phenomenon in the form of a reduction (or loss) of the catalyst amount in the vicinity of the electrolyte membrane occurs. The platinum loss layer is formed as a result of the degradation phenomenon. Since the platinum loss layer is formed in a portion of the catalyst layer close to the electrolyte membrane, the proton transfer distance in the catalyst layer is extended or increased, resulting in an increase of resistance to proton transfer, and reduction of the performance of the fuel cell.

In the case where the reduction of the output performance of the fuel cell is due to the cause (1) as described above (namely, in the case of flooding), for example, when the water-repellent property of carbon that supports platinum deteriorates, and water formed in the cell is less likely to be discharged from the membrane electrode assembly, the water may reduce the reaction field in the cathode, thus causing a reduction of the cell voltage. In this case, control for reducing the humidity (e.g., control for increasing the amount of reaction gas supplied) is effectively performed. In the case where the reduction of the output performance of the fuel cell is due to the cause (2) as described above, there is no need to per-form control concerning the humidity. In the case where the reduction of the output performance of the fuel cell is due to the cause (3) as described above, control for increasing the humidity of the fuel cell (e.g., control for humidifying the fuel cell with a humidifying module, control for lowering the gas inflow pressure, control for reducing the amount of reaction gas supplied) is effectively performed so as to prevent reduction of the cell voltage. Thus, it is necessary to determine the necessity to control the humidity and control the humidity if necessary, with respect to each of the causes (1), (2), (3) of the reduction of the fuel cell output performance.

Although the cause (1) of the reduction of the fuel cell output performance is detected only through measurements of the output voltage and output current, it is extremely difficult to detect the causes (2) and (3) of the reduction of the fuel cell output performance while distinguishing them from each other, since the cell resistance does not change in either of the cases where the causes (2) and (3) occur. The cell resistance does not change for the following two reasons: (1) if even a single particle of the platinum catalyst particles remains in the platinum loss layer, an electron conduction path is formed, and the cell resistance does not change (this situation does not appear in DC resistance), and (2) if there is a humidity distribution in the cell plane, the resistance of a portion having the lowest resistance in the plane is reflected by the cell resistance.

FIG. 4 is a graph showing examples of calculation results indicating prediction results obtained in the fuel cell catalyst degradation predicting step of the invention. In the graph of FIG. 4, the vertical axis indicates the platinum catalyst surface area per unit thickness of the catalyst layer, and the horizontal axis indicates or specifies the position taken in the thickness direction of the catalyst layer where the position of the interface with the electrolyte membrane is denoted as 0, and the position of the interface with the gas diffusion layer is denoted as 1. In FIG. 4, black diamond plots indicate surface areas of the platinum catalyst at respective positions in the initial period of the operating time, and white square plots, black triangle plots, white circle plots, and black square plots indicate surface areas of the platinum catalyst after a lapse of a certain amount of time the fuel cell is used, in increasing order of the operating time of the fuel cell. Also, in the examples of the calculation results, a threshold value of platinum catalyst surface area is determined in advance, and a portion of the catalyst layer below the threshold value is regarded as a platinum loss layer, as shown in FIG. 4. As is understood from FIG. 4, the platinum catalyst surface area that is kept at an equally high value in the catalyst layer during the initial period of the operating time (black diamond plots) starts rapidly decreasing, particularly at around the interface with the electrolyte membrane, as the operating time increases (white square plots→black triangle plots→white circle plots→black square plots). As the platinum catalyst surface area decreases, the thickness of the platinum loss layer rapidly increases at around the interface with the electrolyte membrane. Calculation for estimating the platinum catalyst surface area distribution in the thickness direction of the catalyst layer may be conducted each time a given operating time elapses (for example, once every 100 hours). Namely, the calculation is not necessarily required for each operation. A resistance overvoltage is developed depending on the thickness of the platinum loss layer. The resistance overvoltage may be calculated in advance, using a formula like the following equation (8), for example, and may be used for feedback control.

$$\Delta W = I^2 \times R_{Pt\text{-}loss} \times L \tag{8}$$

(where, $\Delta W$: output reduction (W) caused by the platinum loss layer, I: current (A), $R_{Pt\text{-}loss}$: resistance ($\Omega/cm^2$) per unit area of the platinum loss layer, and L: thickness (cm) of the platinum loss layer.)

The method of controlling the fuel cell according to the invention has the fuel cell catalyst deterioration predicting step, cell voltage measuring step, cell resistance measuring step, step of determining whether humidity control is to be performed (which will be called "humidity control execution determining step), and a step (which will be called "humidity control executing step") of effecting a selected one of different control modes, based on the result of determination obtained in the humidity control execution determining step. Of these steps, the fuel cell catalyst degradation predicting step has already been described above in the explanation of the fuel cell catalyst degradation predicting method of the invention. Also, known methods of the related art may be used as a method of measuring the cell voltage of the fuel cell in the cell voltage measuring step and a method of measuring the cell resistance of the fuel cell in the cell resistance measuring step. In the following, the humidity control execution determining step and the humidity control executing step will be described in detail.

In the humidity control execution determining step of the invention, it is determined whether humidity control is to be performed, based on the result of degradation prediction obtained in the fuel cell catalyst degradation predicting step, the value of cell voltage obtained in the cell voltage measuring step, and the value of cell resistance obtained in the cell resistance measuring step. For example, the measured cell voltage V is compared with a predetermined threshold value $V_1$. If $V<V_1$, for example, it is found that some abnormality occurs in the fuel cell, and the performance of the fuel cell is reduced due to the abnormality. Also, the measured cell resistance R is compared with a predetermined $R_1$ (the minimum value in a permissible range of cell resistance). If $R<R_1$, it may be determined that flooding occurs (which is the cause (1) of reduction of the output performance of the fuel cell), and that control for reducing the humidity needs to be performed. Furthermore, the measured cell resistance R is compared with a predetermined $R_2$ (the maximum value in the permissible range of cell resistance). If $R>R_2$, it may be determined that the increase of the resistance value occurs due to drying or low humidity, and that control for increasing the humidity needs to be performed. Also, if a reduction of the surface area in a local portion of the fuel cell catalyst can be predicted from the result of prediction of degradation obtained in the fuel cell catalyst degradation predicting step, it may be determined that voltage reduction occurs due to the presence of the platinum loss layer (the cause (3) of reduction of the output performance of the fuel cell), and it may be determined that control for increasing the humidity needs to be performed. In contrast to this case, if it can be predicted that the surface area of the fuel cell catalyst is not locally reduced, it may be determined that voltage reduction occurs due to reduction of the surface area of the platinum catalyst (the cause (2) of reduction of the output performance of the fuel cell), and it may be determined that humidity control is not particularly needed. While it may be determined whether humidity control needs to be performed, by individually evaluating the degradation prediction result obtained in the fuel cell catalyst degradation predicting step, the value of cell voltage obtained in the cell voltage measuring step, and the value of cell resistance obtained in the cell resistance measuring step, these prediction result and measurement values may be comprehensively evaluated or assessed so as to determine whether the humidity control needs to be performed.

In the humidity control executing step of the invention, a control mode may be selected from at least the first control mode in which control for reducing the humidity is performed, and the second and third control modes in which control for increasing the humidity is performed, according to the circumstances, and the selected control mode may be carried out. A specific method of controlling the humidity is not particularly limited. Rather, different control methods may be used depending on the control mode selected, or, even in the same control mode, the humidity may be controlled by different control methods according to the circumstances. Specific examples of the method of controlling the humidity include, for example, control using a humidifying module, control of the gas inflow pressure, control of the amount of reaction gas supplied, and control of the flow rate of the coolant. In particular, the coolant flow rate control is performed so as to control the cell temperature, thereby to indirectly control the humidity. In the first control mode, at least one control selected from control for increasing the gas inflow pressure, control for increasing the amount of reaction gas supplied, and control for reducing the flow rate of the coolant (namely, control for raising the cell temperature) is performed so as to reduce the humidity. In the second and third control modes, at least one control selected from control for reducing the gas inflow pressure, control for reducing the amount of reaction gas supplied, and control for increasing the flow rate of the coolant (namely, control for lowering the cell temperature) is performed so as to increase the humidity.

Figure 5:
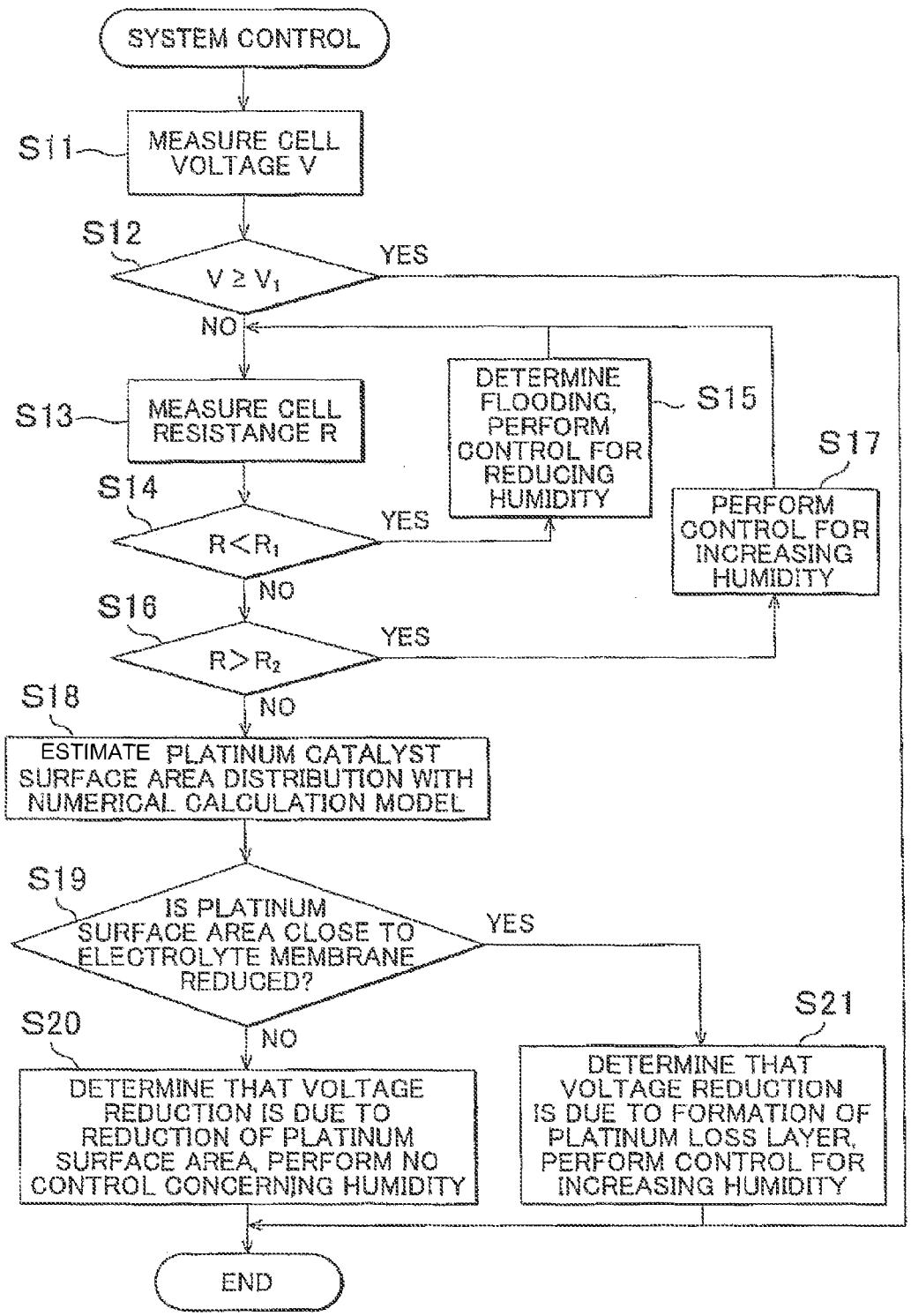
FIG. 5 is a flowchart illustrating a typical example of a method of controlling a fuel cell according to the invention.

FIG. 5 is a flowchart illustrating a typical example of the method of controlling the fuel cell according to the invention. Initially, the cell voltage V is measured in step S11 as shown in FIG. 5, and the measured cell voltage V is compared with a predetermined threshold value $V_1$ in step S12. The control ends if V is equal to or larger than $V_1$, and the control proceeds to step S13 if V is smaller than $V_1$. The cell resistance is measured in step S13, and the measured cell resistance R is compared with a predetermined threshold value $R_1$ (the maximum value in a permissible range of the cell resistance) in step S14. If R is smaller than $R_1$, it is determined that flooding occurs (which is the cause (1) of reduction of the output performance of the fuel cell), and the first control mode is selected in which control for reducing the humidity is performed (step S15). After the control for reducing the humidity is performed, the control returns to step S13, and the first control mode is selected to keep the humidity reduction control performed until the resistance value R becomes equal to or larger than $R_1$. If it is determined in step S14 that R is equal to or larger than $R_1$, the control proceeds to step S16. In step S16, the measured cell resistance R is compared with a predetermined threshold value $R_2$ (the maximum value in the permissible range of cell resistance). If R is larger than $R_2$, the second control mode is selected in which control for increasing the humidity is performed (step S17). After the control for increasing the humidity is performed, the control returns to step S13, and the second control mode is selected to keep the control for increasing the humidity performed until the resistance value R becomes equal to or larger than $R_1$ and equal to or smaller than $R_2$ ($R_1 \leq R \leq R_2$). If it is determined in step S16 that R is equal to or smaller than $R_2$, the control proceeds to step S18. In step S18, it is predicted whether the surface area of a portion of the platinum catalyst close to the electrolyte membrane is reduced, using the degradation prediction result obtained in the fuel cell catalyst degradation predicting step. For the prediction, the graph of examples of calculation results as shown in FIG. 4 may be used. If it is predicted from the graph that the surface area of the fuel cell catalyst is locally reduced, more specifically, the surface area of a portion of the platinum catalyst close to the electrolyte membrane is reduced, it is determined that the voltage reduction is due to the presence of the platinum loss layer (which is the cause (3) of reduction of the output performance of the fuel cell), and the third control mode in which control for increasing the humidity is performed is selected so as to increase the humidity (step S21). If it is predicted that the surface area of the fuel cell is not locally reduced, more specifically, the surface area of a portion of the platinum catalyst close to the electrolyte membrane is not reduced, it is determined that the voltage reduction is due to reduction of the surface area of the platinum catalyst (which is the cause (2) of reduction of the output performance of the fuel cell), and no particular control concerning the humidity is performed (step S20). After execution of step S20 or step S21, the system control ends.

While specific embodiments of the invention will be described in further detail, it is to be understood that the invention is not limited to these embodiments, but may be otherwise embodied without departing from the principle of the invention.

A particle size distribution model was created, using the particle size distribution model creating method of the invention. To create the model, Microsoft Office Excel (trade name, manufactured by Microsoft) was used as spreadsheet software, and the NORMINV function that returns values of the inverse function of the cumulative distribution function of a normal distribution with respect to the designated average and standard deviation was used as the function. The NORMINV function has three arguments of NORMINV(probability x, average μ, standard deviation σ).

To create a particle size distribution model 1, a particle size range was determined in which the minimum particle size is 1.9 (in nm, the same unit will be used for other particle sizes), and the maximum particle size is 3.1. The average particle size was 2.5. Then, the determined particle range was divided into 10 regions. More specifically, x=0.1, 0.2, 0.3, . . . 0.9, μ=2.5, and standard deviation σ=0.2 were respectively substituted into the NORMINV function, and 9 division points were determined by calculating a value of $F(X)^{-1}$ for each probability, namely, values of the inverse function of the cumulative distribution function. The results of calculation are indicated in TABLE 2 below.

TABLE 2

| x | $F(x)^{-1}$ |
|---|---|
| 0.1 | 2.2437 |
| 0.2 | 2.3317 |
| 0.3 | 2.3951 |
| 0.4 | 2.4493 |
| 0.5 | 2.5000 |
| 0.6 | 2.5507 |
| 0.7 | 2.6049 |
| 0.8 | 2.6683 |
| 0.9 | 2.7563 |

The values of 1.9 (minimum particle size) and 3.1 (maximum particle size) were added to the values of these division points, so that a total of 11 typical points were determined. With the thickness in the actual catalyst layer further taken into consideration, the particle size distribution model 1 was created. In this example, 10 layers of the particle size distribution models each having particles sizes of the above-indicated 11 typical points were superimposed in the direction of thickness of the catalyst layer, to create the model (TABLE 3). Namely, this model has a uniform particle size distribution as viewed in the direction of thickness of the catalyst layer.

TABLE 3

| | z (Mesh in Thickness Direction of Catalyst Layer) | | | | | | | | | |
|---|---|---|---|---|---|---|---|---|---|---|
| | 1 | 2 | 3 | 4 | 5 | 6 | 7 | 8 | 9 | 10 |
| 1 | 1.9 | 1.9 | 1.9 | 1.9 | 1.9 | 1.9 | 1.9 | 1.9 | 1.9 | 1.9 |
| 2 | 2.2437 | 2.2437 | 2.2437 | 2.2437 | 2.2437 | 2.2437 | 2.2437 | 2.2437 | 2.2437 | 2.2437 |
| 3 | 2.3317 | 2.3317 | 2.3317 | 2.3317 | 2.3317 | 2.3317 | 2.3317 | 2.3317 | 2.3317 | 2.3317 |
| 4 | 2.3951 | 2.3951 | 2.3951 | 2.3951 | 2.3951 | 2.3951 | 2.3951 | 2.3951 | 2.3951 | 2.3951 |
| 5 | 2.4493 | 2.4493 | 2.4493 | 2.4493 | 2.4493 | 2.4493 | 2.4493 | 2.4493 | 2.4493 | 2.4493 |
| 6 | 2.5000 | 2.5000 | 2.5000 | 2.5000 | 2.5000 | 2.5000 | 2.5000 | 2.5000 | 2.5000 | 2.5000 |
| 7 | 2.5507 | 2.5507 | 2.5507 | 2.5507 | 2.5507 | 2.5507 | 2.5507 | 2.5507 | 2.5507 | 2.5507 |
| 8 | 2.6049 | 2.6049 | 2.6049 | 2.6049 | 2.6049 | 2.6049 | 2.6049 | 2.6049 | 2.6049 | 2.6049 |
| 9 | 2.6683 | 2.6683 | 2.6683 | 2.6683 | 2.6683 | 2.6683 | 2.6683 | 2.6683 | 2.6683 | 2.6683 |
| 10 | 2.7563 | 2.7563 | 2.7563 | 2.7563 | 2.7563 | 2.7563 | 2.7563 | 2.7563 | 2.7563 | 2.7563 |
| 11 | 3.1 | 3.1 | 3.1 | 3.1 | 3.1 | 3.1 | 3.1 | 3.1 | 3.1 | 3.1 |

To create a particle size distribution model 2, a particle size range was determined in which the minimum particle size is 1.4, and the maximum particle size is 2.6. The average particle size was 2. Then, the determined particle range was divided into 10 regions. More specifically, x=0.1, 0.2, 0.3, ... 0.9, $\mu=2$ (in nm, a preferable value as the catalyst particle size), and standard deviation $\sigma=0.2$ were respectively substituted into the NORMINV function, and 9 division points were determined by calculating a value of $F(X)^{-1}$ for each probability, namely, values of the inverse function of the cumulative distribution function. The results of calculation are indicated in TABLE 4 below.

TABLE 4

| x | $F(X)^{-1}$ |
|---|---|
| 0.1 | 1.7436 |
| 0.2 | 1.8316 |
| 0.3 | 1.8952 |
| 0.4 | 1.9494 |
| 0.5 | 2 |
| 0.6 | 2.0506 |
| 0.7 | 2.1048 |
| 0.8 | 2.1684 |
| 0.9 | 2.2564 |

Also, the determined particle size range was divided into 80 regions. More specifically, x=0.0125, 0.0250, 0.0375, ... 0.9875, $\mu=2$ (in nm, a preferable value as the catalyst particle size), and standard deviation $\sigma=0.2$ were respectively substituted into the NORMINV function, and 79 division points were determined by calculating a value of $F(X)^{-1}$ for each probability, namely, values of the inverse function of the cumulative distribution function. The results of calculation are indicated in TABLE 5 below.

TABLE 5

| x | $F(X)^{-1}$ |
|---|---|
| 0.0125 | 1.5517 |
| 0.0250 | 1.6080 |
| 0.0375 | 1.6439 |
| 0.0500 | 1.6710 |
| 0.0625 | 1.6932 |
| 0.0750 | 1.7121 |
| 0.0875 | 1.7287 |
| 0.1000 | 1.7437 |
| 0.1125 | 1.7573 |
| 0.1250 | 1.7699 |
| 0.1375 | 1.7817 |
| 0.1500 | 1.7927 |
| 0.1625 | 1.8032 |
| 0.1750 | 1.8131 |

TABLE 5-continued

| x | $F(X)^{-1}$ |
|---|---|
| 0.1875 | 1.8226 |
| 0.2000 | 1.8317 |
| 0.2125 | 1.8404 |
| 0.2250 | 1.8489 |
| 0.2375 | 1.8571 |
| 0.2500 | 1.8651 |
| 0.2625 | 1.8729 |
| 0.2750 | 1.8804 |
| 0.2875 | 1.8879 |
| 0.3000 | 1.8951 |
| 0.3125 | 1.9022 |
| 0.3250 | 1.9092 |
| 0.3375 | 1.9161 |
| 0.3500 | 1.9229 |
| 0.3625 | 1.9296 |
| 0.3750 | 1.9363 |
| 0.3875 | 1.9428 |
| 0.4000 | 1.9493 |
| 0.4125 | 1.9558 |
| 0.4250 | 1.9622 |
| 0.4375 | 1.9685 |
| 0.4500 | 1.9749 |
| 0.4625 | 1.9812 |
| 0.4750 | 1.9875 |
| 0.4875 | 1.9937 |
| 0.5000 | 2.0000 |
| 0.5125 | 2.0063 |
| 0.5250 | 2.0125 |
| 0.5375 | 2.0188 |
| 0.5500 | 2.0251 |
| 0.5625 | 2.0315 |
| 0.5750 | 2.0378 |
| 0.5875 | 2.0442 |
| 0.6000 | 2.0507 |
| 0.6125 | 2.0572 |
| 0.6250 | 2.0637 |
| 0.6375 | 2.0704 |
| 0.6500 | 2.0771 |
| 0.6625 | 2.0839 |
| 0.6750 | 2.0908 |
| 0.6875 | 2.0978 |
| 0.7000 | 2.1049 |
| 0.7125 | 2.1121 |
| 0.7250 | 2.1196 |
| 0.7375 | 2.1271 |
| 0.7500 | 2.1349 |
| 0.7625 | 2.1429 |
| 0.7750 | 2.1511 |
| 0.7875 | 2.1596 |
| 0.8000 | 2.1683 |
| 0.8125 | 2.1774 |
| 0.8250 | 2.1869 |
| 0.8375 | 2.1968 |
| 0.8500 | 2.2073 |
| 0.8625 | 2.2183 |
| 0.8750 | 2.2301 |
| 0.8875 | 2.2427 |

TABLE 5-continued

| x | F(X)⁻¹ |
|---|---|
| 0.9000 | 2.2563 |
| 0.9125 | 2.2713 |
| 0.9250 | 2.2879 |
| 0.9375 | 2.3068 |
| 0.9500 | 2.3290 |
| 0.9625 | 2.3561 |
| 0.9750 | 2.3920 |
| 0.9875 | 2.4483 |

Finally, with regard to the calculation results of TABLE 4 in which the determined particle size range was divided into 10 regions, the region including the maximum particle size, namely, the section where the value of the particle size is between 2.2564 and 2.6, was replaced by a part (data in the form of boldface and underlined numbers in TABLE 5) of the calculation results of TABLE 5 in which the determined particle size range was divided into 80 regions. Namely, through this operation, the particle size range from 1.4 as the minimum particle size to 2.6 as the maximum particle size was divided into 10 regions, and the region or range including the maximum particle size was further divided into 8 regions. Accordingly, a total of 16 division points were determined as shown in TABLE 6 below.

TABLE 6

| x | F(X)⁻¹ |
|---|---|
| 0.1 | 1.7436 |
| 0.2 | 1.8316 |
| 0.3 | 1.8952 |
| 0.4 | 1.9494 |
| 0.5 | 2 |
| 0.6 | 2.0506 |
| 0.7 | 2.1048 |
| 0.8 | 2.1684 |
| 0.9 | 2.2564 |
| 0.9125 | 2.2713 |
| 0.925 | 2.2879 |
| 0.9375 | 2.3068 |
| 0.95 | 2.329 |
| 0.9625 | 2.3561 |
| 0.975 | 2.392 |
| 0.9875 | 2.4483 |

The values of 1.4 (minimum particle size) and 2.6 (maximum particle size) were added to the values of these division points, so that a total of 18 typical points were determined. Thus, the particle distribution model 2 containing particles having the particle sizes of the typical points was created.

Figure 6A:
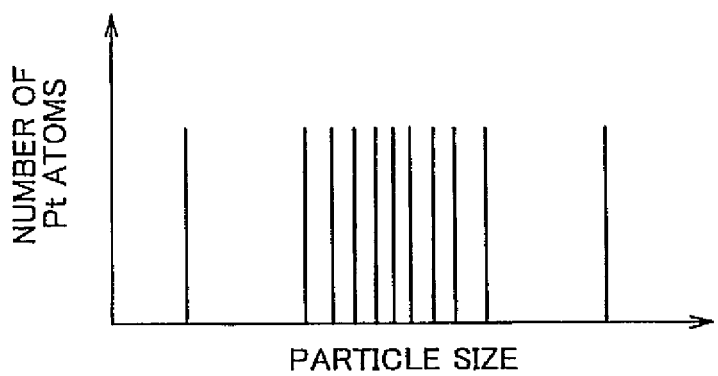
FIG. 6A is a schematic view of a platinum catalyst particle size distribution model used in an embodiment of the invention.
Figure 6B:
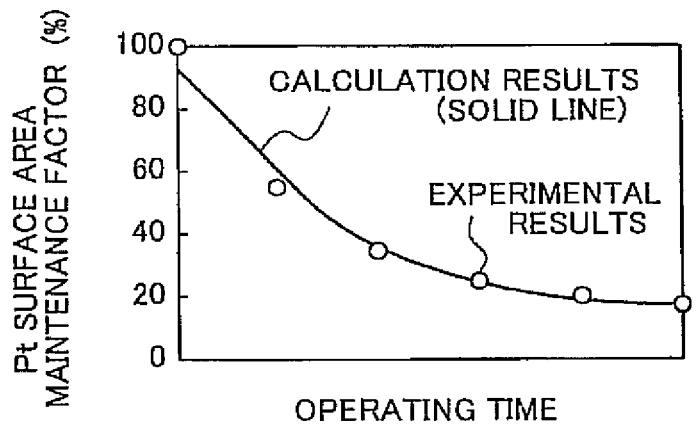
FIG. 6B is a graph indicating the platinum surface area maintenance factor with respect to the operating time (the number of power generation cycles)

Using the method of predicting degradation of the fuel cell catalyst according to the invention, the platinum surface area maintenance factor with respect to the operating time (the number of power generation cycles) was calculated. In this embodiment, the particle size distribution model as shown in TABLE 3 was used as a particle size distribution model of the platinum catalyst in the initial state. FIG. 6A is a schematic view of the distribution mode. For calculation of the platinum surface area maintenance factor, mathematical software (gPROMS) was used. By entering various parameters including equations, boundary conditions, the initial catalyst particle size, the structure of the catalyst layer, such as the thickness of the catalyst layer, and the operating pattern, numerical solutions that vary with time were automatically obtained. In this manner, a graph of the platinum surface area maintenance factor with respect to the operating time (the number of power generation cycles) as shown in FIG. 6B was obtained. The calculation time was about 20 minutes.

As a comparative example, a particle size distribution model in which the same difference in the particle size is taken as equal intervals and the number of particles is a variable was created, separately from the particle size distribution models of the above embodiments of the invention. TABLE 7 below indicates the particle sizes (nm) of the particle size distribution model of the comparative example, and the ratio of the number of particles having one of these particle sizes to a total number of the particles. FIG. 8A is a schematic view of the distribution model. Using the particle size distribution model as shown in FIG. 8A, degradation of the fuel cell catalyst was predicted, and the platinum surface area maintenance factor with respect to the operating time (the number of power generation cycles) was calculated.

TABLE 7

| Particle Size (nm) | Ratio |
|---|---|
| 2.0 | 0.0026613 |
| 2.1 | 0.0134476 |
| 2.2 | 0.0474085 |
| 2.3 | 0.1166061 |
| 2.4 | 0.2000968 |
| 2.5 | 0.2395594 |
| 2.6 | 0.2000968 |
| 2.7 | 0.1155061 |
| 2.8 | 0.0474085 |
| 2.9 | 0.0134476 |
| 3.0 | 0.0026613 |

For calculation of the platinum surface area maintenance factor, mathematical software (gPROMS) was used. By entering various parameters including equations, boundary conditions, the initial catalyst particle size, the structure of the catalyst layer, such as the thickness of the catalyst layer, and the operating pattern, numerical solutions that vary with time were automatically obtained. In this manner, a graph of the platinum surface area maintenance factor with respect to the operating time (the number of power generation cycles) as shown in FIG. 8B was obtained. The calculation time was about 20 minutes.

As is understood from FIG. 6B, the calculation results (solid line in FIG. 6B) of the embodiment of the invention almost precisely simulate the experimental results (plots on the graph); it is thus found that the method of predicting degradation of the fuel cell catalyst according to the invention makes it possible to precisely simulate degradation of the fuel cell catalyst which would occur in reality. In contrast to this, as is understood from FIG. 8B, the calculation results (solid line in FIG. 8B) of the comparative example exhibit poor preciseness in the simulation of the experimental results (plots on the graph), as compared with the calculation results of the embodiment of the invention.

What is claimed is:

1. A computer implemented method of controlling a fuel cell, comprising:
 a fuel cell catalyst degradation predicting step of predicting, using a computer, degradation of a fuel cell catalyst, using a method of predicting degradation of a fuel cell catalyst;
 a cell voltage measuring step of measuring a cell voltage of a fuel cell;
 a cell resistance measuring step of measuring a cell resistance of the fuel cell;
 a humidity control determining step of determining, using the computer, whether humidity control is to be performed, based on a result of degradation prediction obtained in the fuel cell catalyst degradation predicting step, a value of the cell voltage obtained in the cell voltage measuring step, and a value of the cell resistance obtained in the cell resistance measuring step; and a step of selecting, using the computer, a first humidity control mode, a second humidity control mode, or a third humidity control mode based on a determination result obtained in the humidity control determining step, and performing the selected control mode, wherein the first humidity control mode in which control for reducing a humidity is performed is selected and performed when the value of the cell resistance obtained in the cell resistance measuring step is smaller than a value in a predetermined range, the second humidity control mode in which control for increasing the humidity is performed is selected and performed when the value of the cell resistance obtained in the cell resistance measuring step is a value that exceeds a value in the predetermined range, and the third humidity control mode in which control for increasing the humidity is performed is selected and performed when it is predicted that a surface area of a local portion of the fuel cell catalyst is reduced based on the result of degradation prediction obtained in the fuel cell catalyst degradation predicting step, wherein the method of predicting degradation of a fuel cell catalyst includes:

a step of creating a particle size distribution model of a fuel cell catalyst using a particle size distribution model creating method of creating the particle size distribution model, the particle size distribution model simulating a particle size distribution of a cluster of particles including a plurality of particles having different particle sizes; and a step of predicting degradation of the fuel cell catalyst, using the particle size distribution model of the fuel cell catalyst, and the particle size distribution model creating method includes:

a particle size range determining step of determining, using the computer, a minimum particle size and a maximum particle size of the particles included in the cluster of particles to be simulated;

an integrating step of integrating, using the computer, frequency of appearance of the particles within a particle size range determined in the particle size range determining step, using the minimum particle size as a starting point and the maximum particle size as an endpoint;

a division point determining step of dividing, using the computer, an integration region obtained in the integrating step into a given number of regions by performing first division, using a value of integral of the frequency of appearance obtained in the integrating step, so that values of integrals obtained for the regions resulting from the first division are equal, and determining particle sizes at the ends of the regions as division points;

a typical point determining step of determining the minimum particle size, the maximum particle size and the particle sizes of the division points, as typical points;

a step of assuming a particle size distribution which contains particles having the particle sizes of the typical points, and is plotted such that frequencies of appearance of the particles having the particle sizes of the typical points are equal to the values of integrals obtained for the regions defined by the typical points; and a step of obtaining the assumed particle size distribution as a particle size distribution model.

2. The method of controlling a fuel cell according to claim 1, wherein, in the fuel cell catalyst degradation predicting step, at least one mathematical model selected from a mathematical model indicative of a rate of dissolution reaction, a mathematical model indicative of a rate of oxidation reaction, and a mathematical model indicative of material balance is used.

3. The method of controlling a fuel cell according to claim 1, wherein, in the fuel cell catalyst degradation predicting step, all of a mathematical model indicative of a rate of dissolution reaction of platinum, a mathematical model indicative of a rate of oxidation reaction of platinum, a mathematical model indicative of a rate of dissolution reaction of platinum oxide (II), and a mathematical model indicative of material balance are used.

* * * * *